United States Patent [19]

Hungerbach et al.

[11] Patent Number: 5,437,858
[45] Date of Patent: Aug. 1, 1995

[54] ORAL HYGIENE AGENT CONTAINING HYDROGEN PEROXIDE STABILIZED BY COLLOIDAL SILVER

[75] Inventors: Heinz Hungerbach, Merchweiler; Werner Struzina, Heiligenhaus; Albrecht Hoburg, Ratingen, all of Germany

[73] Assignee: Ulrike Hungerbach, Merchweiler, Germany

[21] Appl. No.: 182,050

[22] PCT Filed: Jul. 9, 1992

[86] PCT No.: PCT/EP92/01558

§ 371 Date: Mar. 11, 1994

§ 102(e) Date: Mar. 11, 1994

[87] PCT Pub. No.: WO93/00884

PCT Pub. Date: Jan. 21, 1993

[30] Foreign Application Priority Data

Jul. 13, 1991 [DE] Germany ............... 41 23 292.5

[51] Int. Cl.⁶ ............... A61K 7/20; A61K 33/40; A61K 33/38; A61K 9/68
[52] U.S. Cl. ............... 424/53; 424/48; 424/49; 424/616; 424/618
[58] Field of Search ............... 424/49, 53, 616, 618, 424/48

[56] References Cited

U.S. PATENT DOCUMENTS

| 1,993,686 | 3/1935 | Schulenburg | 87/16 |
| 2,295,505 | 9/1942 | Shelton | 167/22 |
| 3,350,265 | 10/1967 | Rubenstein et al. | 167/338.6 |
| 4,476,108 | 10/1984 | Kesser et al. | 424/53 |
| 4,559,223 | 12/1985 | Fox | 424/49 |
| 4,895,721 | 1/1990 | Drucker | 424/53 |
| 4,915,955 | 4/1990 | Gomori | 424/616 |
| 5,009,898 | 4/1991 | Sakuma et al. | 424/618 |
| 5,084,268 | 1/1992 | Thaler | 424/53 |
| 5,104,644 | 4/1992 | Douglas | 424/53 |

FOREIGN PATENT DOCUMENTS

| 349640 | 4/1979 | Austria . |
| 764670 | 5/1932 | France . |
| 1767605 | 9/1971 | Germany . |
| 2189394 | 10/1987 | United Kingdom . |

*Primary Examiner*—Shep Rose
*Attorney, Agent, or Firm*—Jacobson, Price, Holman & Stern

[57] ABSTRACT

The present application is directed to oral hygiene agents, a process for their preparation, and the use of a hydrogen peroxide solution stabilized by a silver colloid in concentrations of from 0.1 to 10% by weight, preferably from 1 to 3% by weight, in oral hygiene agents.

10 Claims, No Drawings

ORAL HYGIENE AGENT CONTAINING HYDROGEN PEROXIDE STABILIZED BY COLLOIDAL SILVER

This application is a 371 of PCT/EP92/01558 dated Jul. 9, 1992.

This invention is directed to oral hygiene agents, a process for their preparation, and a use.

Hitherto, hydrogen peroxide has been used as bleaching and cleaning agent. The use of hydrogen peroxide for decontaminating and deodorizing water, waste water and exhaust air instead of chlorine dioxide is familiar. For oral disinfection, a 3% hydrogen peroxide solution is suitable.

Use of hydrogen peroxide, particularly in the field of disinfection, gains increasing importance as this substance is considerably more environmentally compatible compared to chlorine-containing disinfectants used so far.

However, usability and storage stability of solutions containing hydrogen peroxide are limited in that hydrogen peroxide, particularly when exposed to heat, light, and in the presence of dust, traces of heavy metals and alkaline substances decomposes more or less rapidly to give water and oxygen. In disinfection or bleaching this is quite a desirable phenomenon since oxygen formed in decomposition has a disinfecting and bleaching effect. When storing such solutions, however, this is disadvantageous since solutions containing hydrogen peroxide decompose after a while and lose their disinfecting effect.

From EP-A-0 325 267, peroxide gels are known which contain from 35 to 95% by weight of polyols and, in addition, a stabilizer and hydrogen peroxide. As stabilizers are mentioned antioxidants or UV-absorbing materials such as butoxylated hydroxyanisole, hydroxytoluene, propyl gallate, or other substituted benzophenones. Although these are said to be toxicologically acceptable, they give rise to problems in part.

From AT-PS 349 640, a toothpaste free of polish is known which substantially consists of an oil-in-water emulsion. Hydrogen peroxide stabilization is effected using urea.

From EP-A-0 288 420, an aqueous hydrogen peroxide gel is known which is gelled with polyoxyethylene/polyoxyproplyene block copolymers and contains polyethylene glycol for moisturizing. The substances utilized therein, in particular Pluronics, are not quite toxicologically safe.

Therefore, it was the technical problem of the invention to provide a stabilized hydrogen peroxide for oral hygiene agents which, on the one hand, permits production of usable and storage-stable oral hygiene agents and, on the other hand, has the familiar advantageous disinfecting effect of hydrogen peroxide.

This technical problem is solved by an oral hygiene agent containing, in addition to common ingredients, a silver colloid-stabilized hydrogen peroxide solution in concentrations of from 0.1 to 10% by weight, preferably from 1 to 3% by weight. Such a stabilized hydrogen peroxide solution is available, for instance, from the company Hungerbach-Chemotechnik GmbH under the designation HUWA-SAN. This solution is stabilized by a silver colloid.

The oral hygiene agent of the invention is prepared by mixing common ingredients with said stabilized hydrogen peroxide solution.

Furthermore, the technical problem of the invention is solved by using a silver colloid-stabilized hydrogen peroxide solution for oral hygiene in concentrations of from 0.1 to 10% by weight, preferably from 1 to 3% by weight.

The silver colloid-stabilized hydrogen peroxide solution may be utilized in a variety of oral hygiene agents including toothpaste, toothpaste for sensitive teeth generally containing soluble potassium and strontium salts or hydroxylapatite, mouth wash, dental powder, and chewing gum for dental care. Furthermore, utilization in oral hygiene agents for artificial teeth such as adhesives, adhesive foams and cleaning agents for artificial teeth is possible. The stabilized hydrogen peroxide solution may also be used as a concentrate or a ready-for-use solution to fill up oral douches.

Despite stabilization, outstanding disinfecting effect is obtained by using the silver colloid-stabilized hydrogen peroxide solution. Thus, the disinfecting effect of a stabilized $H_2O_2$ solution (HUWA-SAN) was investigated. Here, it was determined that effective disinfection in clinical water-bearing systems may be achieved by using stabilized hydrogen peroxide.

Furthermore, a disinfection test was carried out using various germs and various concentrations of stabilized hydrogen peroxide (HUWA-SAN). As can be seen from table 1, no growth can be detected in any strain with concentrations of up to 0.0075%. On the basis of these results, the stabilized hydrogen peroxide solution has significant bacteriostatic and fungistatic activity. The minimum concentration for inhibition is about 5 ppm. On the average, a value for all germs of 30 ppm may be expected.

TABLE 1

Concentration-dependent germ inhibition by stabilized hydrogen peroxide solution (HUWA-SAN)

| Tested germ | Employed germ content/ml | Testing concentration in % | | | | | | | | |
|---|---|---|---|---|---|---|---|---|---|---|
| | | 10 | 1 | 0.1 | 0.05 | 0.01 | 0.0075 | 0.005 | 0.002 | 0.001 | 0.0005 |
| Escherichia coli | $53 \cdot 10^6$ | — | — | — | — | — | — | — | — | — | (+) |
| Klebsiella pneumoniae | $6.1 \cdot 10^6$ | — | — | — | — | — | — | — | — | — | + |
| Staphylococcus | $50 \cdot 10^6$ | — | — | — | — | — | — | — | — | — | |
| Pseudomonas aeruginosa | $70 \cdot 10^6$ | — | — | — | — | — | — | — | + | ++ | ++ |
| Streptococcus faecalis | $36 \cdot 10^6$ | — | — | — | — | — | — | — | — | — | (+) |
| Proteus mirabilis | $24 \cdot 10^6$ | — | — | — | — | — | — | — | — | — | — |
| Mycobacterium tuberculosis | $1.5 \cdot 10^6$ | — | — | — | — | — | (+) | + | + | + |

TABLE 1-continued

Concentration-dependent germ inhibition by stabilized hydrogen peroxide solution (HUWA-SAN)

| Tested germ | Employed germ content/ml | \multicolumn{10}{c}{Testing concentration in %} |
|---|---|---|---|---|---|---|---|---|---|---|---|
| | | 10 | 1 | 0.1 | 0.05 | 0.01 | 0.0075 | 0.005 | 0.002 | 0.001 | 0.0005 |
| Clostridium sporogenes | $2.1 \cdot 10^6$ | — | — | — | — | — | — | — | + | ++ | ++ |
| Candida albicans | $3.2 \cdot 10^6$ | — | — | — | — | — | — | (+) | ++ | ++ | ++ |

Key to symbols:
— = no growth
(+) = faint growth
+ = significant growth
++ = massive growth
BLW = Control value with sterile water In another study, the disinfecting effect in oral hygiene agents was determined using a 2% stabilized hydrogen peroxide solution (HUWA-SAN). Here, the germs Pseudomonas aeruginosa, Candida albicans and Stapihylococcus aureus were used. For testing, plastic plates of prosthetic plastic having a size of 2.5 cm×2.5 cm×0.3 cm were produced. The test specimen were microbially contaminated using following contamination solution:

| | |
|---|---|
| 10 ml | of 0.9% sterile sodium chloride solution with the centrifugate of a 200 ml breed of one of the cultures, |
| 83 ml | of 5% sterile mucin solution, |
| 2 ml | of 5% sterile calcium chloride solution. |

The test specimen were placed into the contamination solution for 30 seconds. They were taken out using a pair of forceps and subsequently laid onto a fine-meshed grid. There, first drying was effected for 15 minutes at room temperature. The contaminated test specimen were foamed from all sides using adhesive foam which was spread using a sterile glass spatula. After the periods of exposure had elapsed, the test specimen were placed onto a sterile cloth of cotton using a pair of forceps and were freed from adhering foam.

The number of germs was determined by shaking out into the following extraction solution:
Substances in 100 ml of CSL
3% of Tween 80
3% of saponine
0.1% of histidine
0.1% of cysteine.

After 2 minutes of shaking, the germ count was performed. After an exposure period of 1 minute, there was found germ reduction for

| | |
|---|---|
| Pseudomonas aeruginosa | to 2% |
| Candida albicans | to 0.06% |
| Staphylococcus aureus | to 0%. |

From these results, very good disinfecting activity of the stabilized hydrogen peroxide solutions can be derived. Further results can be seen from table 2.

TABLE 2

Investigations concerning inhibiting effect in a foam formulation, 2% hydrogen peroxide solution (HUWA-SAN).

| Test specimen | \multicolumn{4}{c}{Period of exposure (minutes)} |
|---|---|---|---|---|
| | 0.5 | 1 | 1.5 | 3 |
| \multicolumn{5}{c}{Test germ: Pseudomonas aeruginosa, $1 \cdot 10^9$ colony-forming units per ml} |
| I | $2.5 \cdot 10^5$ | $4.5 \cdot 10^4$ | $1.5 \cdot 10^4$ | 0 |
| II | $3 \cdot 10^5$ | $5 \cdot 10^4$ | $2 \cdot 10^4$ | 0 |
| III | $3 \cdot 10^5$ | $4 \cdot 10^4$ | $1.5 \cdot 10^4$ | 0 |
| Control | $2.9 \cdot 10^6$ | $2.2 \cdot 10^6$ | $2.2 \cdot 10^6$ | $2.1 \cdot 10^6$ |
| Reduction to about | 10% | 2% | 8% | 0 |
| \multicolumn{5}{c}{Test germ: Candida albicans, $5.5 \cdot 10^8$ colony-forming units per ml} |
| I | $3 \cdot 10^3$ | $1 \cdot 10^3$ | $6 \cdot 10^2$ | $1 \cdot 10^1$ |
| II | $3.5 \cdot 10^3$ | $2 \cdot 10^3$ | $8 \cdot 10^2$ | 0 |
| II | $5 \cdot 10^3$ | $9 \cdot 10^2$ | $8.5 \cdot 10^2$ | 0 |
| Control | $1.9 \cdot 10^6$ | $2 \cdot 10^6$ | $7 \cdot 10^5$ | $1 \cdot 10^5$ |
| Reduction to about | 0.2% | 0.06% | 0.1% | 0.003% |
| \multicolumn{5}{c}{Test germ: Staphylococcus aureus, $2 \cdot 10^9$ colony-forming units per ml} |
| I | $4 \cdot 10^1$ | 0 | $3 \cdot 10^1$ | 0 |
| II | $2 \cdot 10^1$ | 0 | 0 | 0 |
| III | $3.5 \cdot 10^1$ | 0 | $1 \cdot 10^1$ | 0 |
| Control | $3.5 \cdot 10^6$ | $3.7 \cdot 10^6$ | $3.7 \cdot 10^6$ | $3.3 \cdot 10^6$ |
| Reduction to about | 0.0009% | 0 | 0.0003% | 0 |

The further examples demonstrate preferred embodiments of the invention:

EXAMPLE 1

Mouthwash Formulation

In conventional manner, there are mixed
7 wt.-% of ethanol,
17 wt.-% of sorbitol solution
2 wt.-% of stabilized $H_2O_2$ solution (HUWA-SAN)
1 wt.-% of common additives
73 wt.-% of water.

EXAMPLE 2

Adhesive Foam

There are mixed
1 wt.-% of Polyisosorbat 20
0.45 wt.-% of mint oils
5 wt.-% of alcohol
2.20 wt.-% of sodium benzoate
3 wt.-% of sodium lauryl sulfate
5 wt.-% of propane/butane
2 wt.-% of stabilized hydrogen peroxide solution (HUWA-SAN)
1 wt.-% of common additives
80.35 wt.-% of water.

EXAMPLE 3

Toothpaste A 12 wt.-% of diatomaceous earth
1.6 wt.-% of hydroxyethylcellulose
12 wt.-% of glycerol
2 wt.-% of silica
12 wt.-% of sorbitol/xylitol solution
10 wt.-% of strontium chloride
1 wt-.% of peppermint oil
2 wt.-% of stabilized hydrogen peroxide solution (HUWA-SAN)
5 wt.-% of common additives
42.4 wt.-% of water.

EXAMPLE 4

Toothpaste B 5 wt.-% of potassium nitrate
1 wt.-% of sodium monofluorophosphate
36 wt.-% of dicalcium phosphate
12 wt.-% of sorbitol/xylitol solution
12 wt.-% of glycerol
1 wt-.% of peppermint oil
2 wt.-% of stabilized hydrogen peroxide solution (HUWA-SAN)
5 wt.-% of common additives
38 wt.-% of water.

We claim:

1. In a hydrogen-peroxide-containing oral hygiene-composition, the improvement wherein the hydrogen peroxide is silver-colloid-stabilized hydrogen peroxide present at a concentration of 0.1 to 10% by weight.

2. The oral hygiene composition according to claim 1, characterized in that the concentration of said stabilized hydrogen peroxide is from 1 to 3% by weight.

3. The composition according to claim 1, characterized in that the oral hygiene composition is toothpaste, mouthwash, dental powder, dental adhesive, cleaning agent for artificial teeth, chewing gum for dental care, or an oral douche.

4. The composition according to claim 2, characterized in that the oral hygiene composition is toothpaste, mouthwash, dental powder, dental adhesive, cleaning agent for artificial teeth, chewing gum for dental care, or an oral douche.

5. A method of using a silver-colloid-stabilized hydrogen peroxide solution comprising adding the solution to an oral hygiene composition, at a concentration of from 0.1 to 10% by weight.

6. The method according to claim 5, characterized in that the stabilized hydrogen peroxide solution is added at a concentration of from 1 to 3% by weight.

7. The method according to claim 5, characterized in that the oral hygiene composition is toothpaste, mouthwash, dental powder, dental adhesive, cleaning agent for artificial teeth, chewing gum for dental care, or an oral douche.

8. The method according to claim 6, characterized in that the oral hygiene composition is toothpaste, mouthwash, dental powder, adhesive, cleaning agent for artificial teeth, chewing gum for dental care, or an oral douche.

9. The method of claim 5, wherein the composition is toothpaste comprising a soluble potassium salt, a soluble strontium salt, or hydroxyapatite.

10. The method of claim 6, wherein the composition is toothpaste comprising a soluble potassium salt, a soluble strontium salt, or hydroxyapatite.

* * * * *